US009383343B2

(12) United States Patent
Mitsumura et al.

(10) Patent No.: US 9,383,343 B2
(45) Date of Patent: Jul. 5, 2016

(54) STRENGTH EVALUATING METHOD FOR ALUMINUM DIE CAST PART, ALUMINUM DIE CAST PART, AND DEFECT DETECTING METHOD FOR THE SAME

(75) Inventors: Munetaka Mitsumura, Fujisawa (JP); Shigeru Okita, Fujisawa (JP)

(73) Assignee: NSK Ltd., Tokyo (JP)

( * ) Notice: Subject to any disclaimer, the term of this patent is extended or adjusted under 35 U.S.C. 154(b) by 419 days.

(21) Appl. No.: 13/581,185

(22) PCT Filed: Oct. 28, 2011

(86) PCT No.: PCT/JP2011/006058
§ 371 (c)(1),
(2), (4) Date: Sep. 10, 2013

(87) PCT Pub. No.: WO2012/117468
PCT Pub. Date: Sep. 7, 2012

(65) Prior Publication Data
US 2013/0340562 A1  Dec. 26, 2013

(30) Foreign Application Priority Data

| Feb. 28, 2011 | (JP) | 2011-042505 |
| Sep. 29, 2011 | (JP) | 2011-214392 |
| Oct. 11, 2011 | (JP) | 2011-223939 |
| Oct. 19, 2011 | (JP) | 2011-229785 |

(51) Int. Cl.
*G01N 29/44* (2006.01)
*B62D 1/16* (2006.01)
(Continued)

(52) U.S. Cl.
CPC .............. *G01N 29/4445* (2013.01); *B62D 1/16* (2013.01); *C22C 21/00* (2013.01); *G01N 3/20* (2013.01);
(Continued)

(58) Field of Classification Search
CPC . G01N 29/4445; G01N 23/046; G01N 29/07; G01N 3/20; G01N 2223/419; G01N 2291/0289; G01N 2203/0658; B62D 1/16
USPC ............................................................ 73/601
See application file for complete search history.

(56) References Cited

U.S. PATENT DOCUMENTS

| 4,469,164 A * | 9/1984 | Ishikawa ................ B22D 17/32 164/151.1 |
| 4,843,884 A * | 7/1989 | House .................... G01N 29/26 73/622 |

(Continued)

FOREIGN PATENT DOCUMENTS

| CN | 1040437 A | 3/1990 |
| JP | 56-74650 A | 6/1981 |

(Continued)

OTHER PUBLICATIONS

Written Opinion of the International Searching Authority dated Mar. 19, 2013 (forms PCT/IB/310 PCT/ISA/237) (five (5) pages).

(Continued)

*Primary Examiner* — J M Saint Surin
(74) *Attorney, Agent, or Firm* — Crowell & Moring LLP

(57) ABSTRACT

There is provided an aluminum die cast part strength evaluating method is provided for correctly evaluating strength of an actual aluminum die cast part. Strength of the actual aluminum die cast part will be correctly evaluated by conducting ultrasonic inspection of a predetermined range of a high stress region of an aluminum die cast part, which is found out through stress analysis beforehand, for an internal defect, and evaluating that the aluminum die cast part has a predetermined strength if the maximum internal defect area within the predetermined range is equal to or less than a predetermined value. Moreover, an actual aluminum die cast part with a predetermined strength will be evaluated correctly by: evaluating strength using the aluminum die cast part strength evaluating method and setting the maximum-possible internal defect area within the predetermined range of the high stress region to 0.8 $mm^2$ or less.

4 Claims, 18 Drawing Sheets

(51) Int. Cl.
*C22C 21/00* (2006.01)
*G01N 23/04* (2006.01)
*G01N 29/07* (2006.01)
*G01N 3/20* (2006.01)

(52) U.S. Cl.
CPC .............. *G01N 23/046* (2013.01); *G01N 29/07* (2013.01); *G01N 2203/0658* (2013.01); *G01N 2223/419* (2013.01); *G01N 2291/0289* (2013.01)

(56) References Cited

U.S. PATENT DOCUMENTS

| | | | |
|---|---|---|---|
| 5,028,381 A | 7/1991 | Dugue | |
| 5,954,897 A * | 9/1999 | Ohtake | B60G 7/001 148/439 |
| 5,965,720 A | 10/1999 | Gryaznov et al. | |
| 6,237,713 B1 * | 5/2001 | Onodera | B62D 5/0403 180/443 |
| 6,332,361 B1 * | 12/2001 | Yamada | G01N 29/11 73/598 |
| 7,575,041 B2 * | 8/2009 | Odashima | B22D 11/003 148/551 |
| 8,528,407 B2 * | 9/2013 | Ostapenko | H01L 22/12 73/12.01 |
| 2015/0044090 A1 * | 2/2015 | Mitsumura | B22C 9/24 420/591 |

FOREIGN PATENT DOCUMENTS

| | | |
|---|---|---|
| JP | 59-24215 A | 2/1984 |
| JP | 3-226668 A | 10/1991 |
| JP | 9-325136 A | 12/1997 |
| JP | 10-197500 A | 7/1998 |
| JP | 2004-144289 A | 5/2004 |
| JP | 2005-91288 A | 4/2005 |
| JP | 2005-201330 A | 7/2005 |
| JP | 2007-111728 A | 5/2007 |
| JP | 2007-263579 A | 10/2007 |
| JP | 2009-108095 A | 5/2009 |

OTHER PUBLICATIONS

International Search Report dated Nov. 29, 2011 with English translation (four (4) pages).

Mechanical English translation of document B1 (JP 2005-91288 A) previously filed on Aug. 24, 2012 (nine (9) pages).

Japanese Office Action issued in counterpart Japanese Application No. 2011-223939 dated Feb. 9, 2016 with English translation (six pages).

* cited by examiner

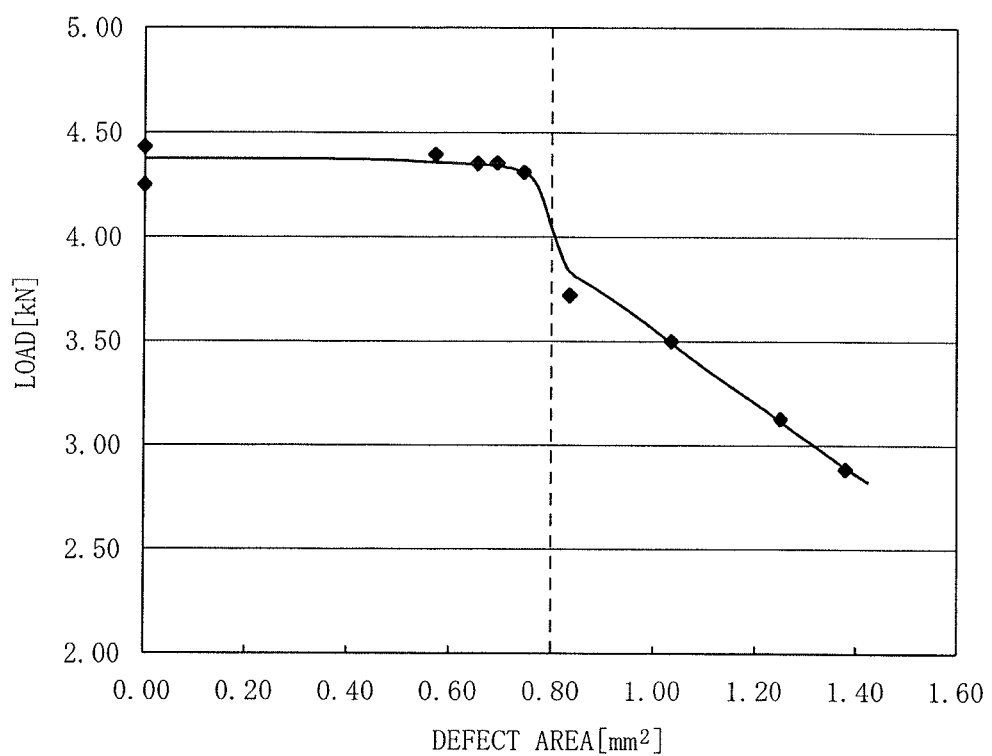
F I G. 10

F I G. 17
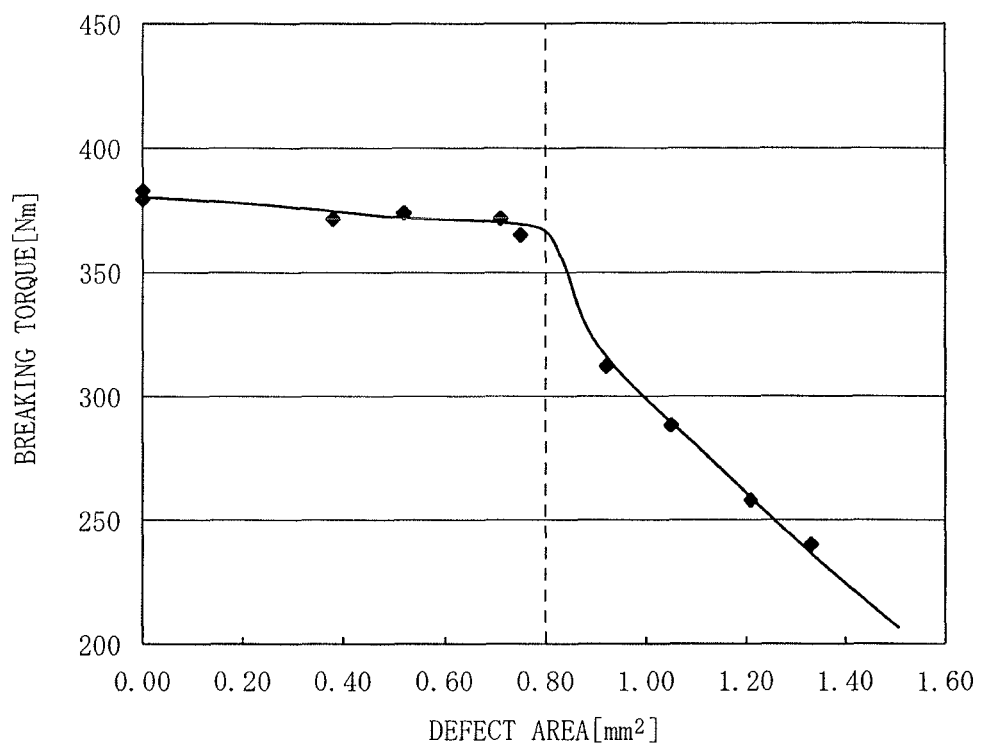

F I G. 19 A
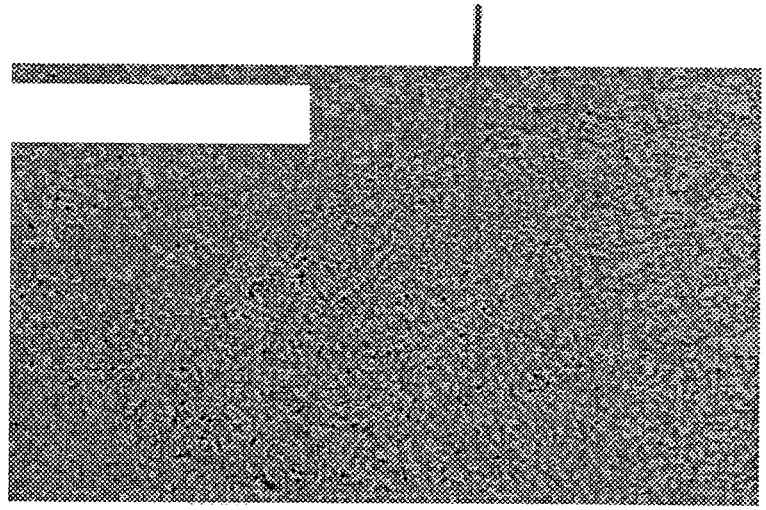
F I G. 19 B

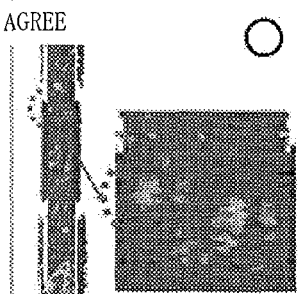
FIG. 20A
FIG. 20B
FIG. 21A          FIG. 21B          FIG. 21C
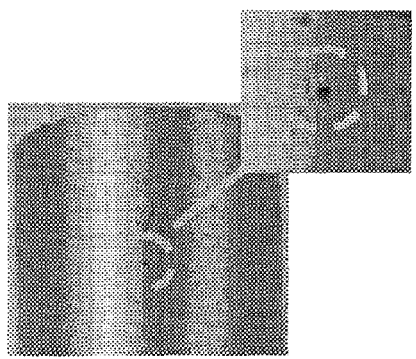 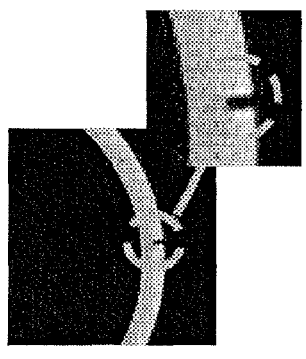 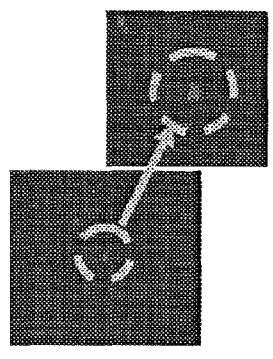

F I G. 22
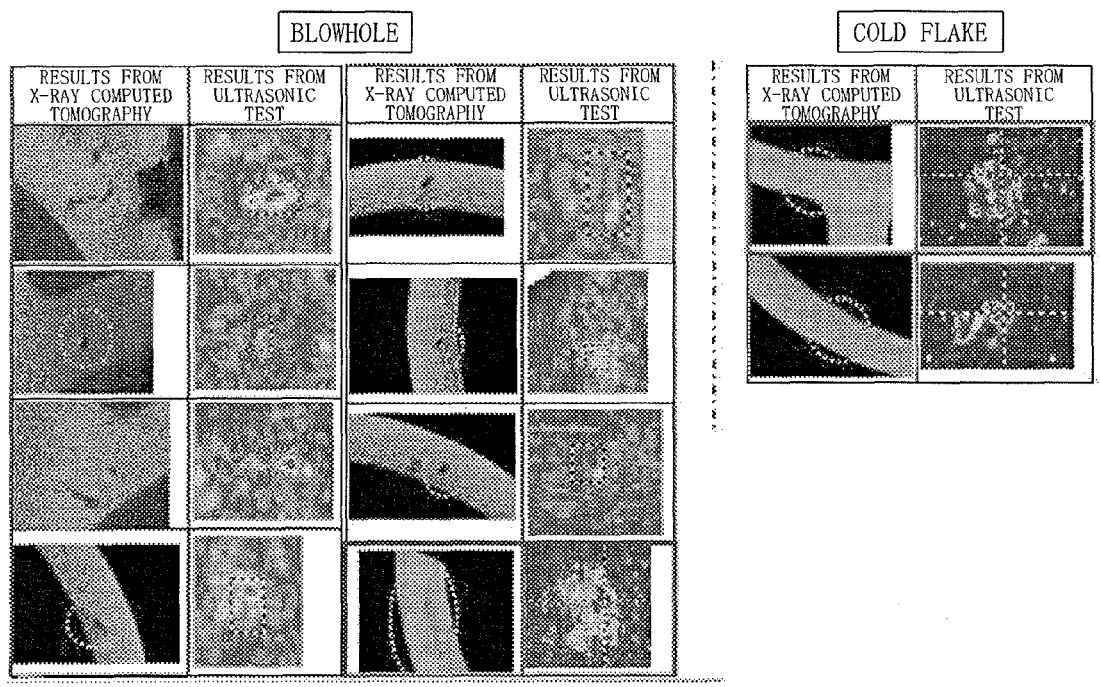

F I G. 23
RESULTS FROM
ULTRASONIC TEST
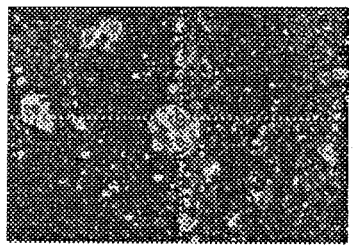
RESULTS FROM
X-RAY COMPUTED TOMOGRAPHY
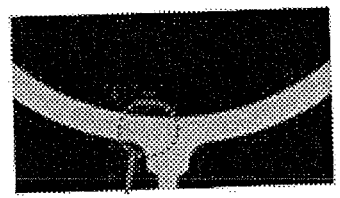
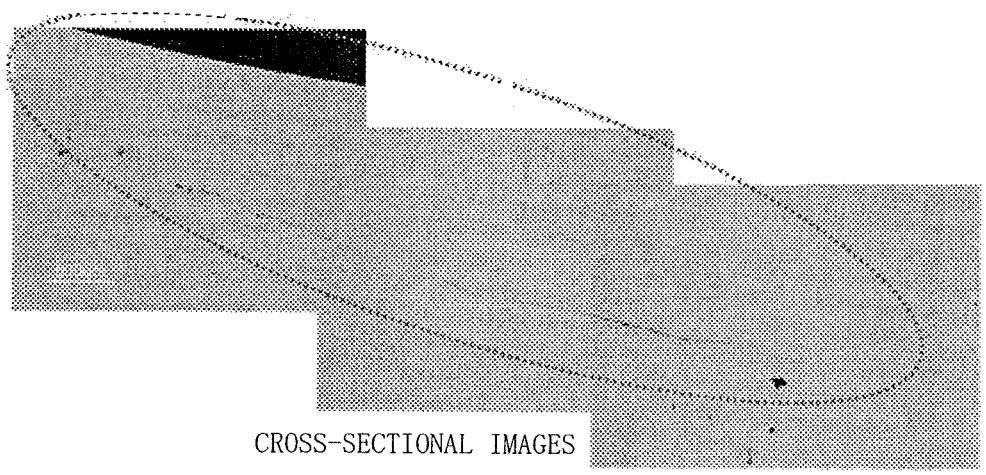
CROSS-SECTIONAL IMAGES F I G. 24A
F I G. 24B
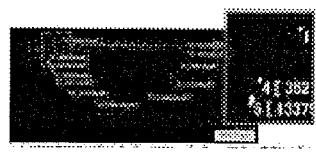
F I G. 24C
| No. | AREA (mm²) |
|---|---|
| 1 | 34 |
| 2 | 28 |
| 3 | 29 |
| 4 | 29 |
| 5 | 106 |
| 6 | 27 |
| 7 | 31 |
| 8 | 23 |
| 9 | 25 |
| 10 | 25 |
| 11 | 51 |
| 12 | 32 |
| TOTAL AREA | 441 |
F I G. 24D
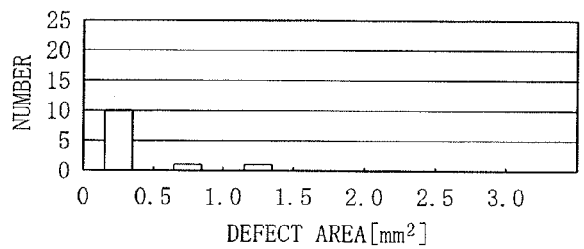
F I G. 24E
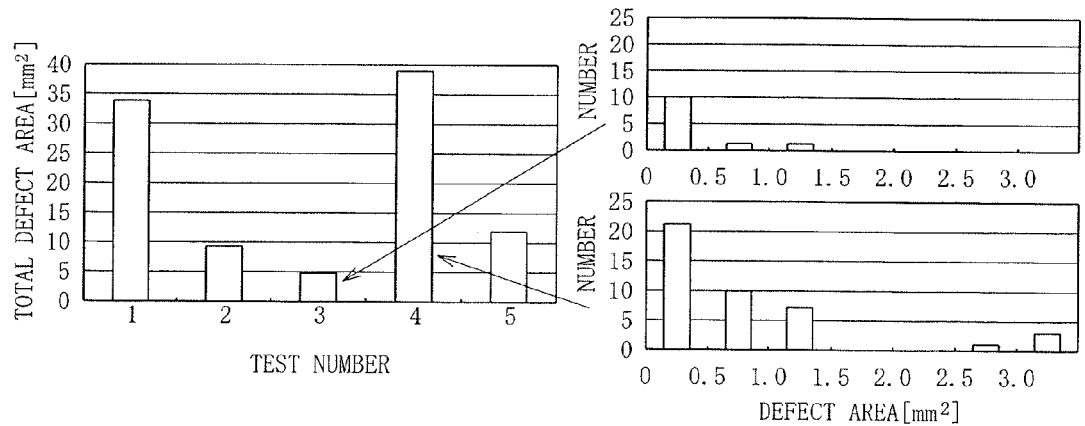

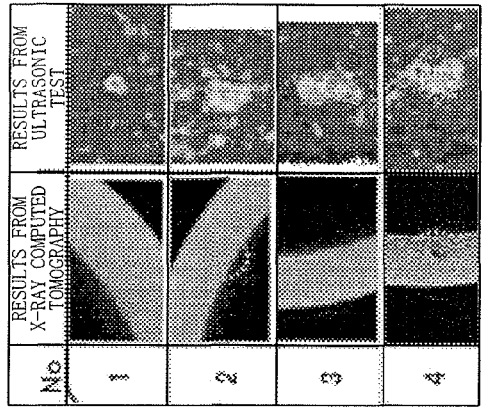
FIG. 25D
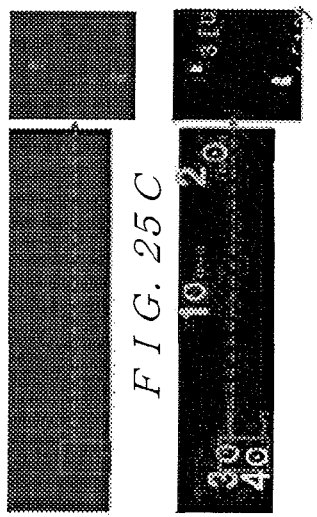
FIG. 25B
FIG. 25C
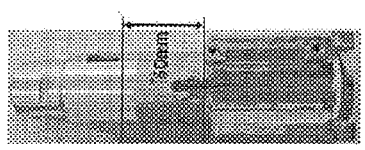
FIG. 25A
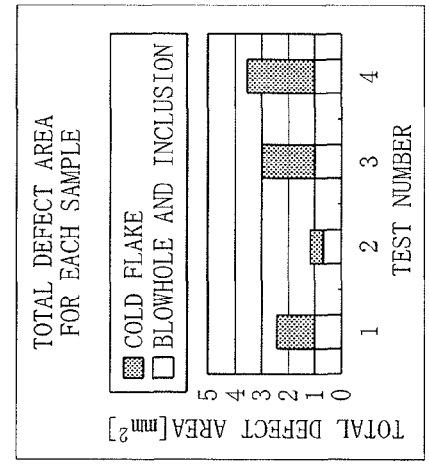
FIG. 25E
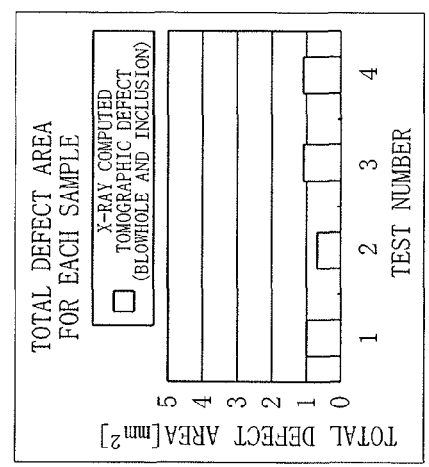
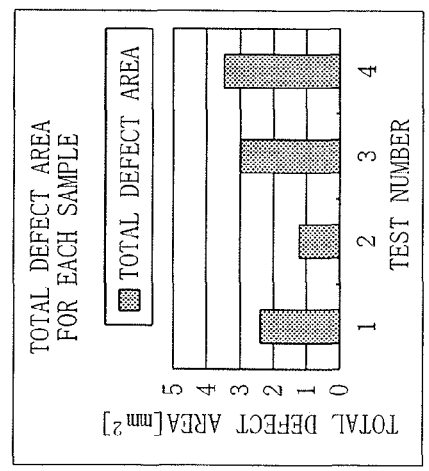

STRENGTH EVALUATING METHOD FOR ALUMINUM DIE CAST PART, ALUMINUM DIE CAST PART, AND DEFECT DETECTING METHOD FOR THE SAME

TECHNICAL FIELD

The present invention relates to a method for evaluating strength of an aluminum die cast part, a defect detecting method for an aluminum die cast part, and an aluminum die cast part, which, for example, are suitable for parts used in an in-vehicle electric power steering apparatus.

BACKGROUND ART

For example, the column housing used for an in-vehicle electric power steering apparatus is made of an aluminum die cast part. For example, such an aluminum die cast part is disclosed in the following Patent Document 1. According to Patent Document 1, reduction in manufacturing cost may be attained with a 5 mm or less thick aluminum die cast part with a HRB50 or greater Rockwell hardness, and even if casting defects arise, a quality aluminum die cast part with high strength may be provided. Moreover, for example, an aluminum die cast part strength evaluating method is disclosed in the following Patent Documents 2 and 3. According to Patent Document 2, for example, three-dimensional distribution data of cold flakes in a casting is obtained by applying a supersonic wave to the casting, detecting a blowhole or a cold flake in the casting based on supersonic-wave information of the casting, acquiring first three-dimensional internal defect distribution data, carrying out X-ray computed tomography on the same casting, detecting a blowhole in multiple cross-sectional images of the casting; acquiring second three-dimensional internal defect distribution data; and comparing the first three-dimensional internal defect distribution data to the second three-dimensional internal defect distribution data. Additionally, according to Patent Document 3, it is determined whether an aluminum die cast part has a defect by cutting down and extracting an inspection piece from a solidified molten metal in a runner near the gate of the aluminum die cast part; calculating an area ratio of the area of the cold flake exposed to the control surface of the extracted inspection piece to the entire area of the control surface, and comparing that ratio with a predetermined reference value.

PRIOR ART DOCUMENTS

Patent Documents

Patent Document 1: JP2009-108095 A
Patent Document 2: JP2005-91288 A
Patent Documents 3: JP2007-111728 A

SUMMARY OF THE INVENTION

Problem to be Solved

However, with the aluminum die cast part disclosed in Patent Document 1, only the strength of a 5 mm or less long specimen can be evaluated, and strength of the actual aluminum die cast part is not evaluated. Furthermore, the aluminum die cast part strength evaluating method disclosed in Patent Document 2 is only for the examination of solidified molten metal in the runner of an aluminum die cast part, and not for examination of the aluminum die cast part itself. On the other hand, the aluminum die cast part strength evaluating method disclosed in Patent Document 1 can evaluate the aluminum die cast part itself. However, it is impossible to examine, for example, the entirety of a large complicated aluminum die cast part practically. An internal defect, such as a blowhole, of an actual aluminum die cast part is unavoidable, and in the end it may be destroyed due to the internal defect. Moreover, since aluminum die cast parts often have a complicated form, it is unclear at which portion strength should be evaluated by ultrasonic internal defect inspection. Moreover, it is very difficult to acquire cold flake distribution data from an actual aluminum die cast part by acquiring three-dimensional internal defect distribution data through ultrasonic inspection, acquiring three-dimensional internal defect distribution data through X-ray computed tomography, and comparing both results.

The present invention is made in light of the problem, and it aims at evaluating an actual aluminum die cast part correctly through ultrasonic inspection. More specifically, it aims at providing a method for evaluating strength of an aluminum die cast part and an aluminum die cast part, which allow proper evaluation of the strength of an actual aluminum die cast part and provision of an aluminum die cast part with a predetermined strength. Moreover, it aims at providing an aluminum die cast part defect detecting method for detecting an internal defect of an actual aluminum die cast part correctly, especially cold flakes.

Solution to the Problem

In order to solve the problem, a method for evaluating strength of an aluminum die cast part according to an aspect of the present invention is characterized in that the method includes conducting ultrasonic inspection for an internal defect in a predetermined range of a high stress region in an aluminum die cast part, which is found through stress analysis beforehand, and evaluating that the aluminum die cast part has a predetermined strength if the maximum internal defect area within the predetermined range is equal to or less than a predetermined value.

Furthermore, a method for evaluating strength of an aluminum die cast part is characterized in that the method includes conducting ultrasonic inspection for an internal defect in a predetermined range of a high stress region; wherein the high stress region is destroyed through a bending test of the aluminum die cast part and found through stress analysis, and then evaluating that the aluminum die cast part has a predetermined strength if the maximum internal defect area within the predetermined range is equal to or less than a predetermined value.

Yet furthermore, an aluminum die cast part according to an aspect of the present invention is characterized in that its strength is evaluated using the aluminum die cast part strength evaluating method; wherein a maximum-possible internal defect area within the predetermined range of the high stress region is 0.8 mm$^2$ or less.

Yet furthermore, the above mentioned aluminum die cast part is preferably a part used for an in-vehicle electric power steering apparatus.

Yet furthermore, the above-mentioned aluminum die cast part is a column housing used for an in-vehicle electric power steering apparatus, wherein the above-mentioned high stress section may be a clamp section of the above-mentioned column housing.

Yet furthermore, a method for evaluating strength of an aluminum die cast part according to an aspect of the present invention is characterized in that the method includes conducting ultrasonic inspection for an internal defect in a predetermined range of a high stress region; wherein the high stress region is destroyed through a bending test of the aluminum die cast part and found through stress analysis; and evaluating that the aluminum die cast part has a predetermined strength if the maximum internal defect within the predetermined range is equal to or less than a predetermined value.

Yet furthermore, an aluminum die cast part according to an aspect of the present invention is characterized in that its strength is evaluated using the aluminum die cast part strength evaluating method; wherein the maximum-possible internal defect area within the predetermined range of the high stress region is set to 0.8 mm² or less.

Yet furthermore, the above-mentioned aluminum die cast part is preferably a part used for an in-vehicle electric power steering apparatus.

Yet furthermore, the above-mentioned aluminum die cast part is a column housing used for an in-vehicle electric power steering apparatus, wherein the above-mentioned high stress section may be a keylock section of the above-mentioned column housing.

Yet furthermore, a method for detecting a detect of an aluminum die cast part according to an aspect of the present invention is characterized in that the method includes adjusting beforehand both outputs of an image obtained through ultrasonic inspection and an image obtained through X-ray computed tomography, so that defect areas corresponding to the same defect in the both images agree with each other; conducting ultrasonic inspection for an internal defect in a predetermined range of an aluminum die cast part; obtaining an internal defect area through image analysis of an internal defect detected through ultrasonic inspection over the predetermined range; calculating a sum total of internal defect areas detected through the ultrasonic inspection over the predetermined range as a sum total of ultrasonic inspected defect areas; conducting X-ray computed tomography for an internal defect over a predetermined range of the aluminum die cast part; calculating an internal defect area through image analysis of the internal defect detected though X-ray computed tomography over the predetermined range; obtaining a sum total of internal defect areas detected through X-ray computed tomography of the predetermined range as a sum total of X-ray computed tomography defect areas; subtracting the sum total of X-ray computed tomography defect areas from sum total of the ultrasonic inspected defect areas; and calculating a sum total of cold flake areas within a predetermined range of the aluminum die cast part.

Yet furthermore, it is preferable that for finding a sum total of internal defect areas obtained through ultrasonic inspection and a sum total of internal defect areas obtained through X-ray computed tomography, a sum total of defect areas, each being equal to or greater than a predetermined area, is calculated.

Yet furthermore, it is preferable that for finding a sum total of internal defect areas obtained through ultrasonic inspection and a sum total of internal defect areas obtained through X-ray computed tomography, a histogram for the number of internal defects within a predetermined defect area range is created.

Advantageous Effect of the Invention

According to an aspect of the present invention, a method for evaluating strength of an aluminum die cast part will provide correct evaluation of the strength of an actual aluminum die casting part by conducting ultrasonic inspection for an internal defect in a predetermined range of a high stress section of the aluminum die cast part found beforehand through stress analysis, and evaluating that the aluminum die casting part has a predetermined strength if the maximum internal defect area within the predetermined range is equal to or less than a predetermined value.

Moreover, the strength of the actual aluminum die casting part can be evaluated correctly because a high stress region of the aluminum die cast part, which has been destroyed through a bending test conducted beforehand and has been stress-analyzed beforehand is subjected to ultrasonic inspection for an internal defect within a predetermined range of the high stress section, and if the maximum internal defect area is equal to or less than a predetermined value, it is evaluated that the aluminum die cast part has a predetermined strength.

Moreover, the strength of the actual aluminum die casting part can be evaluated correctly because a predetermined range of the high stress section of an aluminum die cast part, which has been destroyed through a torsion test conducted beforehand and has been stress analyzed beforehand is detected through stress analysis beforehand, is subjected to ultrasonic inspection for an internal defect, and if the maximum internal defect area within a predetermined range is equal to or less than a predetermined value, it is determined that the aluminum die cast part has a predetermined strength.

Moreover, according to an aspect of the present invention, an aluminum die cast part having a predetermined strength is provided by evaluating its strength using the aluminum die cast part strength evaluating method according to the present invention, and setting a maximum-possible internal defect area within the predetermined range of the high stress region to 0.8 mm² or less.

Moreover, according to an aspect of the present invention, a method for detecting a defect of an aluminum die cast part includes: adjusting beforehand both outputs of an image obtained through the ultrasonic inspection and an image obtained through X-ray computed tomography, so that defected areas corresponding to the same defect in the both images to agree with each other; conducting ultrasonic inspection for an internal defect in a predetermined range of an aluminum die cast part; obtaining an internal defect area through image analysis of the internal defect detected through ultrasonic inspection over the predetermined range; and calculating a sum total of internal defect areas detected through ultrasonic inspection over the predetermined range as a sum total of ultrasonic inspected defect areas. The method further includes: conducting X-ray computed tomography over a predetermined range of the aluminum die cast part for an internal defect; calculating an internal defect area through image analysis of the internal defect detected though X-ray computed tomography over the predetermined range, obtaining a sum total of internal defect areas detected through X-ray computed tomography over the predetermined range as a sum total of X-ray computed tomography defect areas; subtracting the sum total of X-ray computed tomography defect areas from sum total of the ultrasonic inspected defect areas; and calculating a sum total of cold flake areas within a predetermined range of the aluminum die cast part.

An internal defect of the aluminum die cast part, especially the state of a cold flake will thus be detected correctly.

Moreover, in the case of finding a sum total of internal defect areas obtained through ultrasonic inspection and a sum total of internal defect areas obtained through X-ray computed tomography, a sum total of defect areas, each being equal to or greater than a predetermined area, is calculated, thereby correctly detecting an internal defect of the aluminum die cast part, especially the state of a cold flake. Moreover, in the case of finding a sum total of internal defect areas obtained through ultrasonic inspection and a sum total of internal defect areas obtained through X-ray computed tomography, a histogram based on the number of the internal defects within a predetermined defect area range is created, thereby allowing easy recognition of the state of an internal defect of the aluminum die cast part.

BRIEF DESCRIPTION OF THE DRAWINGS

FIG. 10 is a graph showing a relationship between the internal defect area according to the first embodiment and load applied through a bending test;

FIG. 17 is a graph showing a relationship between the internal defect area according to the first embodiment and load applied through a torsion test;

FIGS. 19A and 19B are photographic images of a blowhole and a cold flake in a thin strip-like test piece obtained through ultrasonic inspection and X-ray computed tomography;

FIGS. 20A and 20B are images of a blowhole and a cold flake in a tensile test piece obtained through ultrasonic inspection and X-ray computed tomography, and photographic fracture images;

FIGS. 21A to 21C are images of an artificial defect detected through ultrasonic inspection and X-ray computed tomography, and photographic images thereof;

FIG. 22 are images of a blowhole and a cold flake of an aluminum die cast part obtained though ultrasonic inspection and X-ray computed tomography;

FIG. 23 are images of a cold flake obtained through ultrasonic inspection and X-ray computed tomography, and cross-sectional photographic images thereof;

FIGS. 24A to 24E show images of an internal defect detected through ultrasonic inspection, histograms of defect areas, and a sum total defects or a sum of defect areas; and FIGS. 25A to 25E are views for explaining how to calculate a sum total of cold flakes.

DESCRIPTION OF EMBODIMENTS

Figure 1A:
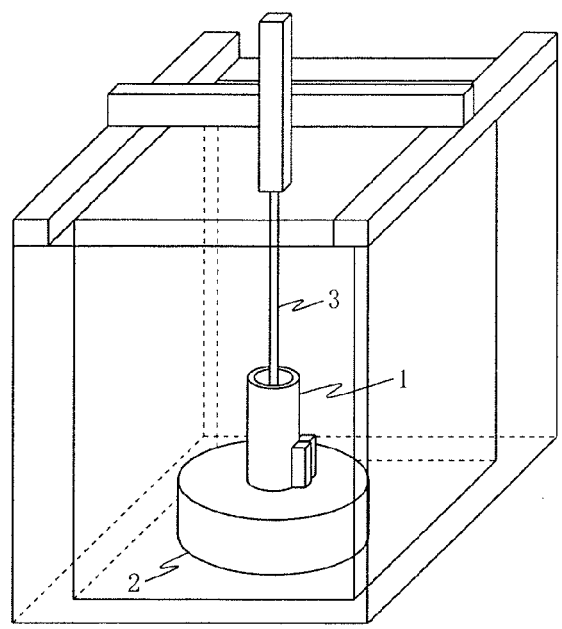
FIGS. 1A to 1C are explanatory views of a first embodiment of an aluminum die cast part strength evaluating method according to the present invention.
Figure 1B:
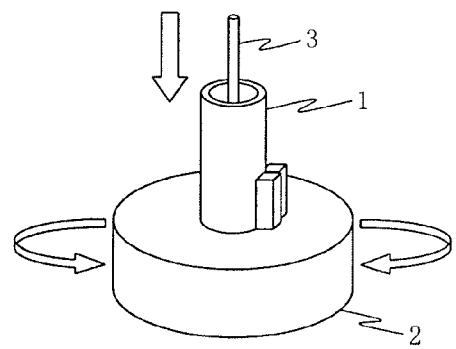
Figure 1C:
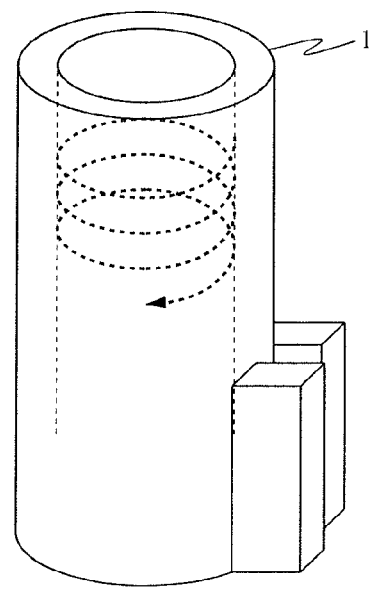

Next, the first embodiment of an aluminum die cast part strength evaluating method according to the present invention will be explained referring drawings. FIGS. 1A to 1C are explanatory views of a movable, six-axis ultrasonic reflectoscope used for an aluminum die cast part strength evaluating method of this embodiment; wherein FIG. 1A is a general view of the ultrasonic reflectoscope, FIG. 1B is detailed view of a subject to be inspected for a defect and a turntable, and FIG. 1C is a explanatory view for internal defect detection. Reference numeral 1 in the views denotes an aluminum die cast part, such as a column housing of an electric power steering apparatus, which is subjected to strength inspection according to the embodiment.

In the embodiment, an aluminum die cast part (column housing) 1 is installed on a turntable 2, and a probe 3 is moved to the lower location from the upper while the turntable 2 is being rotated, thereby spirally inspecting the inside of the aluminum die cast part 1 for a defect. Since the aluminum die cast part (column housing) 1 of the embodiment has a cylindrical section, a high stress region of the cylindrical section is inspected for a defect using an ultrasonic reflectoscope.

Figure 2A:
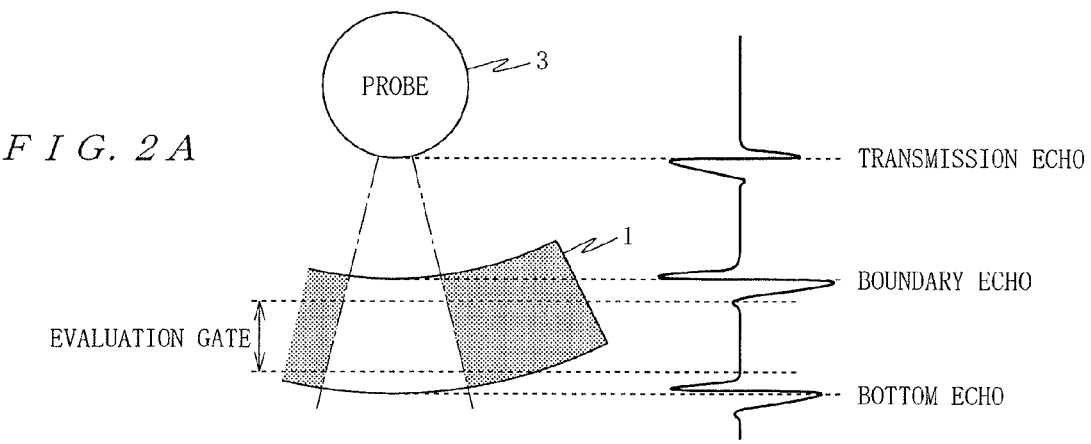
FIGS. 2A and 2B are explanatory views for internal defect detection according to the aluminum die cast part strength evaluating method of FIG. 1.
Figure 2B:
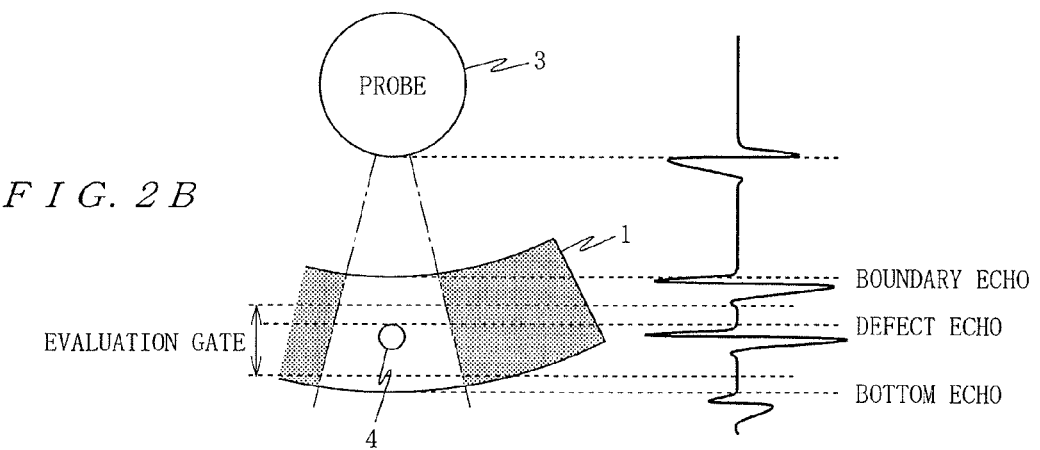

As shown in FIG. 2A, for defect detection, an evaluation gate is set up between a boundary echo and a bottom echo of the aluminum die cast part 1; wherein the evaluation gate denotes a defect detection range. In ultrasonic inspection, supersonic waves oscillated from the probe 3 reflect from the surface and the bottom of the aluminum die cast part 1. The reflected waves serve as the boundary echo and the bottom echo, respectively. As shown in FIG. 2B, if there is an internal defect 4 within a defect detection range of the aluminum die cast part 1, a defect echo should appear in between the boundary and the bottom echo, or within the range of the evaluation gate. Since the time of the boundary echo and time of the bottom echo are known beforehand, an echo existing between the two times must be a defect echo. A technique of viewing the strongest of defect echoes on the inner surface of the aluminum die cast part 1 is used. Note that inner diameter of the cylindrical section of the column housing, which is the aluminum die cast part 1 of the embodiment, is 38 mm, and the defect detection range along the axis of the cylindrical section is set to 90 mm. Moreover, detection of a defect echo may be easier by machining the inner circumference of the cylindrical section of the aluminum die cast part (column housing) 1.

Figure 3:
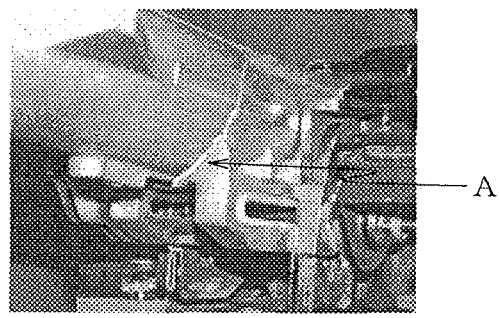
FIG. 3 is a picture showing a destroyed portion of the aluminum die cast part of the first embodiment.
Figure 4:
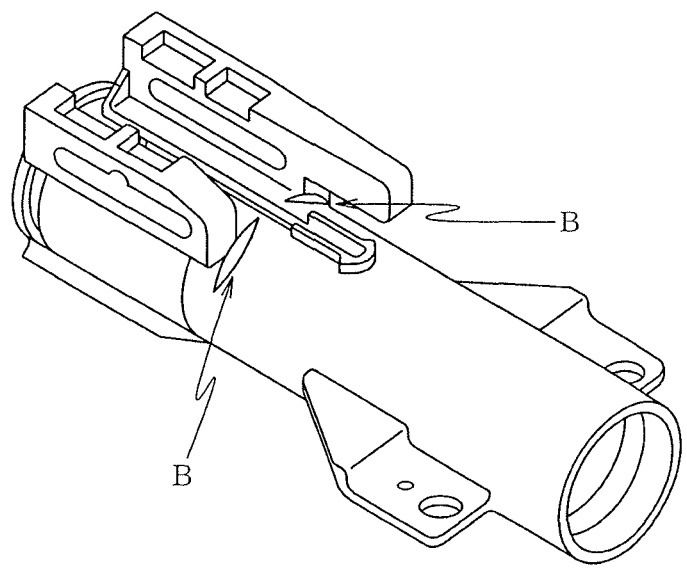
FIG. 4 is an explanatory view of a high stress section of the aluminum die cast part of the first embodiment.

A bending test is carried out on the column housing, i.e., the aluminum die cast part 1, before defect detection. A portion indicated by A in FIG. 3 has been destroyed (cracked) specifically in a clamp section through the bending test. On the other hand, stress analysis of the aluminum die cast part (column housing) 1 has revealed the fact that the clamp section is a high stress region indicated by B in FIG. 4. Through comparison of both results, it is understood that destruction has occurred in the high stress region of the aluminum die cast part 1, i.e., the clamp section of column housing. That is, since destruction emanating from an internal defect, for example, tends to occur on the high stress region (clamp section), we decided to carryout defect detection on the high stress region (clamp section) for an internal defect.

Figure 5:
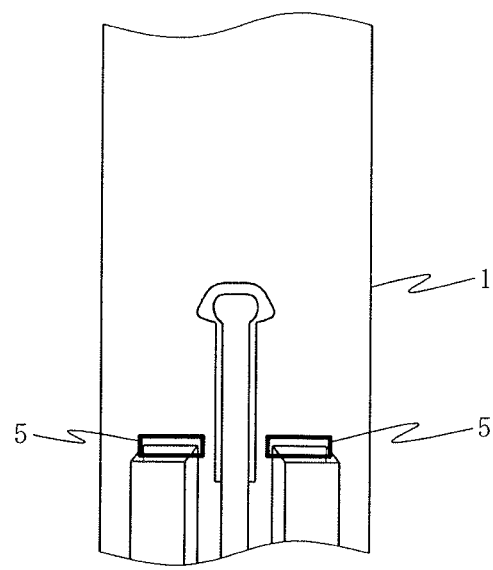
FIG. 5 is an explanatory view of a high stress section of the aluminum die cast part of the first embodiment.
Figure 6:
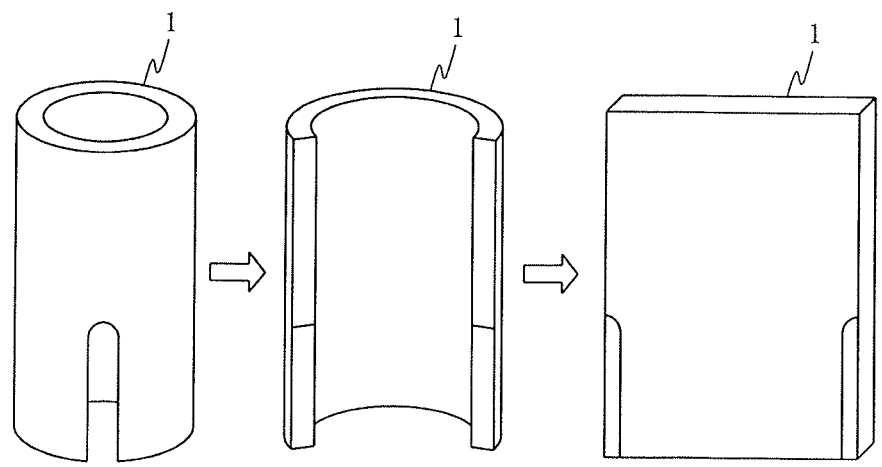
FIG. 6 is explanatory image obtained through internal defect detection shown in FIG. 2, according to the first embodiment.

FIG. 5 shows high stress regions (clamp sections) 5 in the aluminum die cast part (column housing) 1 according to the embodiment. Portions surrounded by respective black rectangles are the high stress sections (predetermined ranges) 5. The inside of the aluminum die cast part (column housing) 1 including these high stress regions (clamp sections) 5 is subjected to ultrasonic inspection, and an internal defect is depicted on a spread image of the inside of the cylindrical section of the aluminum die cast part (column housing) as shown in FIG. 6.

Figure 7A:
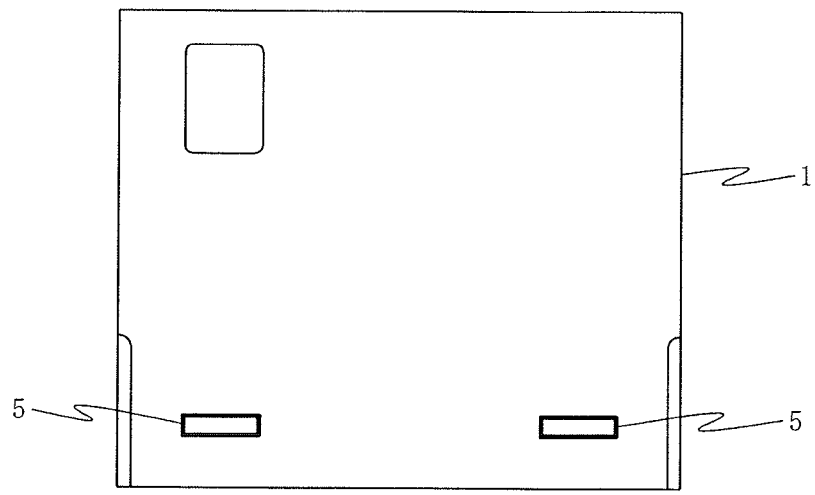
FIGS. 7A and 7B are defect images obtained through internal defect detection shown in FIG. 2, according to the first embodiment.
Figure 7B:
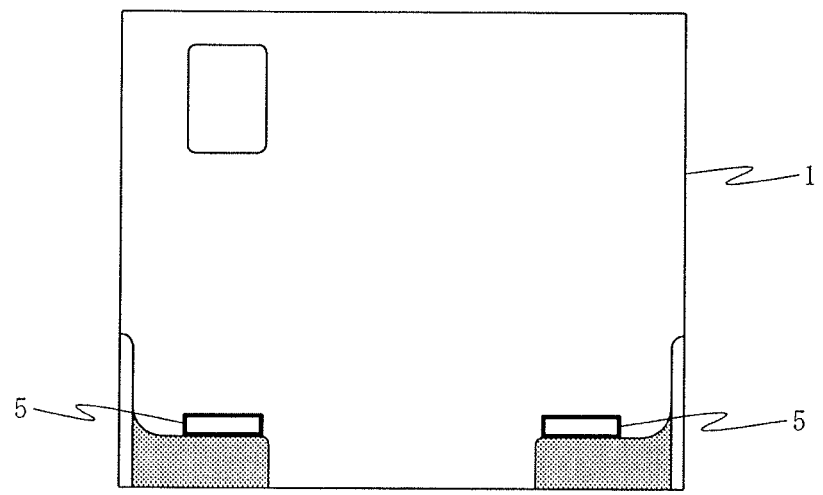
Figure 8:
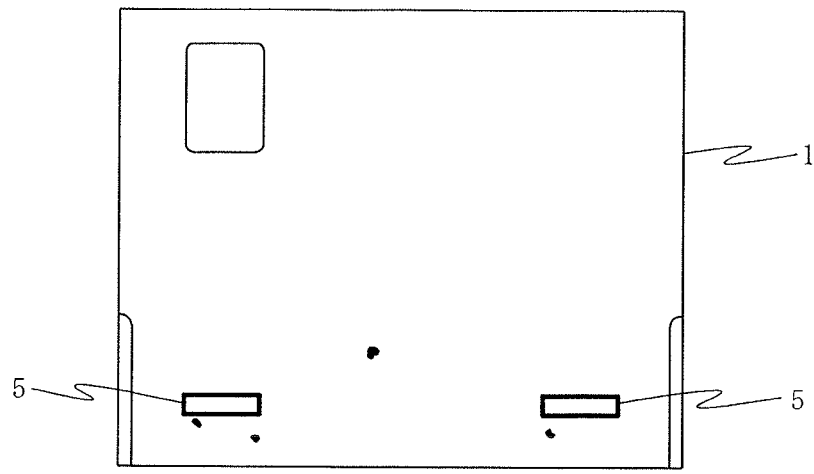
FIG. 8 is a binary image of the defect image obtained through the inspection shown in FIG. 7.
Figure 9:
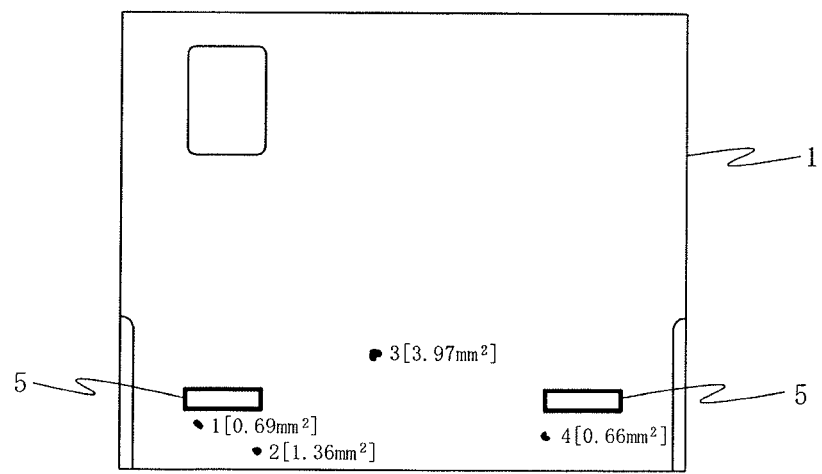
FIG. 9 is a view illustrative of an internal defect area calculated through image analysis of the binary defect image in FIG. 8.

FIGS. 7A and 7B are defect images obtained through ultrasonic inspection; wherein FIG. 7A is a defect image of the central portion along the thickness of the cylindrical section in the aluminum die cast part (column housing) 1 and FIG. 7B is a defect image of the outer surface (top surface in FIG. 4) of the cylindrical section in the aluminum die cast part (column housing) 1. As mentioned above, since the defect detection range is 90 mm along the height and an entirety of the inner circumference of the cylindrical section, the horizontal axis of the image is 119 mm (inner diameter of the inner circumference: 38 mm) while the vertical axis is 90 mm. FIG. 8 is a classified-by-color binary image obtained by binarizing the defect image based on an echo strength threshold of 50% and classifying by color. Black portions in the view include an internal defect with echo strength of no less than 50%. FIG. 9 shows the results from carrying out image analysis of each internal defect area with echo strength of 50% or higher as shown in FIG. 8. Note that it was determined that an internal defect area with 50 pixels or less (area of less than 0.2 mm$^2$) has no problem in strength, and was eliminated from those to be evaluated for an internal defect.

Table 1 below gives all internal defect areas analyzed in that manner. In Table 1, an internal defect existing in the aforementioned high stress section (clamp section) 5 is No. 5. Note that if there are multiple internal defects in the high stress regions (clamp sections) 5, the largest internal defect area will be selected, and the selected area will be evaluated.

TABLE 1

| | Areas with 50 pixels or less are eliminated | | | |
|---|---|---|---|---|
| NO. | area | unit | perimeter | unit |
| 1 | 0.61 | mm$^2$ | 2.85 | mm |
| 2 | 1.26 | mm$^2$ | 5.19 | mm |
| 3 | 0.83 | mm$^2$ | 3.46 | mm |
| 4 | 1.70 | mm$^2$ | 5.04 | mm |
| 5 | 0.74 | mm$^2$ | 3.97 | mm |
| 6 | 0.60 | mm$^2$ | 3.03 | mm |
| 7 | 0.60 | mm$^2$ | 3.12 | mm |
| 8 | 1.03 | mm$^2$ | 3.85 | mm |
| 9 | 1.24 | mm$^2$ | 4.64 | mm |
| 10 | 0.82 | mm$^2$ | 4.30 | mm |
| 11 | 1.70 | mm$^2$ | 5.85 | mm |
| 12 | 0.83 | mm$^2$ | 7.22 | mm |
| Total area | 11.95 | mm$^2$ | | |

In this manner, ten aluminum die cast parts (column housing) 1 are subjected to ultrasonic inspection for an internal defect, and the internal defect area in the high stress regions (clamp sections) 5 is analyzed. Furthermore, a bending test is conducted on those aluminum die cast parts (column housing) 1, thereby detecting a breaking load. Table 2 below gives a relationship between internal defect areas in a high stress region (clamp section) 5 and the breaking load applied through the bending test. Moreover, FIG. 10 is a graph showing the results given in Table 2.

TABLE 2

| | No. | Defect area · [mm$^2$] | Load [kN] |
|---|---|---|---|
| Working example | 1 | 0.00 | 4.25 |
| | 2 | 0.00 | 4.43 |
| | 3 | 0.57 | 4.39 |
| | 4 | 0.65 | 4.35 |
| | 5 | 0.69 | 4.35 |
| | 6 | 0.74 | 4.31 |
| Comparative example | 7 | 0.83 | 3.72 |
| | 8 | 1.03 | 3.50 |
| | 9 | 1.25 | 3.13 |
| | 10 | 1.38 | 2.89 |

As is apparent from FIG. 10, the larger the internal defect area in a high stress region (clamp section) 5, the smaller the breaking load applied through the bending test. That is, the larger the internal defect area in a high stress region (clamp section) 5, the earlier it is destroyed. However, if the internal defect area in the high stress region (clamp section) 5 is 0.8 mm$^2$ or less, an almost constant breaking strength is maintained irrelevant of the internal defect area. Namely, in the case of the aluminum die cast part (column housing) 1 of the embodiment, and if the internal defect area in a high stress region (clamp section) 5 is 0.8 mm$^2$ or less, it can be evaluated that the aluminum die cast part has a predetermined strength.

Moreover, according to observation of a destructive cross-section in an actual aluminum die cast part (column housing,) since a crack has spread from an internal defect, it was determined that there was an internal defect-originated destruction. Therefore, size of an internal defect in the high stress regions (clamp sections) 5, that is, the internal defect area, is detected, and if the internal defect area is equal to or less than a predetermined value, internal defect-originated destruction will be prevented. Therefore, if the internal defect area in the high stress regions (clamp sections) 5 is equal to or less than a predetermined value, it will be appropriate to evaluate that the aluminum die cast part (column housing) 1 has a predetermined strength.

As such, according to an aluminum die cast part strength evaluating method of the embodiment, an internal defect within a predetermined range of each of the high stress sections (clamp sections) 5 of the aluminum die cast part (column housing) 1, which is detected through stress analysis beforehand, is subjected to ultrasonic inspection, and if the maximum internal defect area within the predetermined range is equal to or less than the predetermined value, it is determined that the aluminum die cast part (column housing) 1 has a predetermined strength. Consequently, strength of the actual aluminum die cast part (column housing) 1 will be evaluated correctly.

Moreover, the high stress region (clamp section) 5 of the aluminum die cast part (column housing) 1, which has been destroyed through the bending test and has been stress-analyzed beforehand, goes through ultrasonic inspection for an internal defect within a predetermined range of the high stress sections (clamp sections) 5, and if the maximum internal defect area is equal to or less than a predetermined value, it is determined that the aluminum die cast part (column housing)

1 has a predetermined strength. Consequently, strength of the actual aluminum die cast part (column housing) 1 will thus be evaluated correctly.

Moreover, according to the aluminum die cast part of the embodiment, the aluminum die cast part (column housing) 1 with a predetermined strength will be obtained by evaluating strength using the method for evaluating strength aluminum die cast part according to the embodiment, and setting the maximum-possible internal defect area to 0.8 mm$^2$ or less within a predetermined range of the high stress region 5.

An aluminum die cast part strength evaluating method of a second embodiment according to the present invention is explained referring drawings.

The aluminum die cast part 1 to be evaluated in strength according to the embodiment is a column housing of an electric power steering apparatus, for example, as in the first embodiment. A movable 6-axis ultrasonic reflectoscope according to the method for evaluating strength of an aluminum die cast part of the embodiment, which is the same as in FIG. 1 of the first embodiment, scans spirally and detects an internal defect in a high stress region of the cylindrical section in the aluminum die cast part (column housing) 1 described later. Moreover, the graphic display technique for the evaluation gate and defective echoes and the defect detection range for ultrasonic inspection according to the embodiment are the same as in the first embodiment in FIG. 3.

Figure 11:
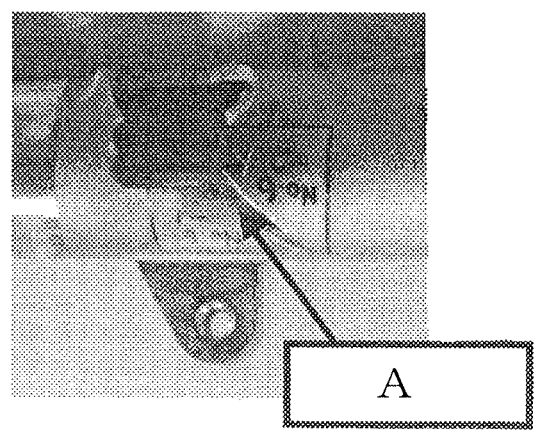
FIG. 11 is a picture showing a destroyed portion of the aluminum die cast part when subjected through a torsion test according to an aluminum die cast part strength evaluating method of a second embodiment according to the present invention.
Figure 12:
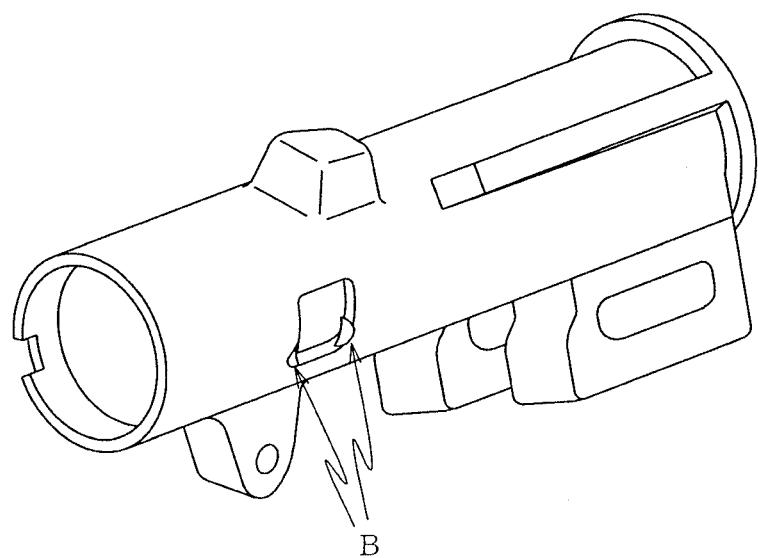
FIG. 12 is an explanatory view of a high stress section of an aluminum die cast part according to the second embodiment.
Figure 13:
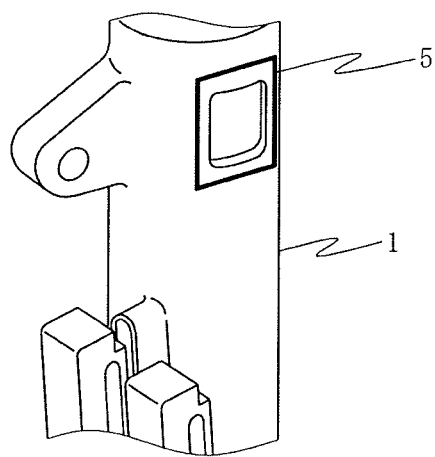
FIG. 13 is an explanatory view of the high stress section of the aluminum die cast part according to the second embodiment.

Prior to defect detection, a key was inserted into a keylock section of the column housing, which is the aluminum die cast part 1, and a breaking torque in which a load was imposed in a twisting direction was conducted in this embodiment. As a result of the torsion test, a defect (crack) developed at a portion A, specifically in a keylock section in FIG. 11. On the other hand, stress analysis of the aluminum die cast part (column housing) 1 under the same load condition as that for the indicates that a portion B, or a keylock section in FIG. 12 is a high stress region. Comparison of both of them indicates that destruction has occurred in the high stress region of the aluminum die cast part 1, that is, the keylock section in the column housing. Namely, since the high stress region (keylock section) tends to develop destruction easily due to an internal defect, we have decided to check high stress region, for internal defects In FIG. 13, a high stress region (keylock section) 5 of the aluminum die cast part (column housing) 1 according to the embodiment is shown. A portion within a black rectangle in the view denotes the high stress region (keylock section) 5. The inner portion of the aluminum die cast part (column housing) 1 including this high stress region (keylock section) 5 is subjected to ultrasonic inspection, and the aluminum die cast part (column housing) 1 is cut along a slit as in the first embodiment in FIG. 6, and an internal defect is graphically displayed on the view along the spread inner portion.

Figure 14:
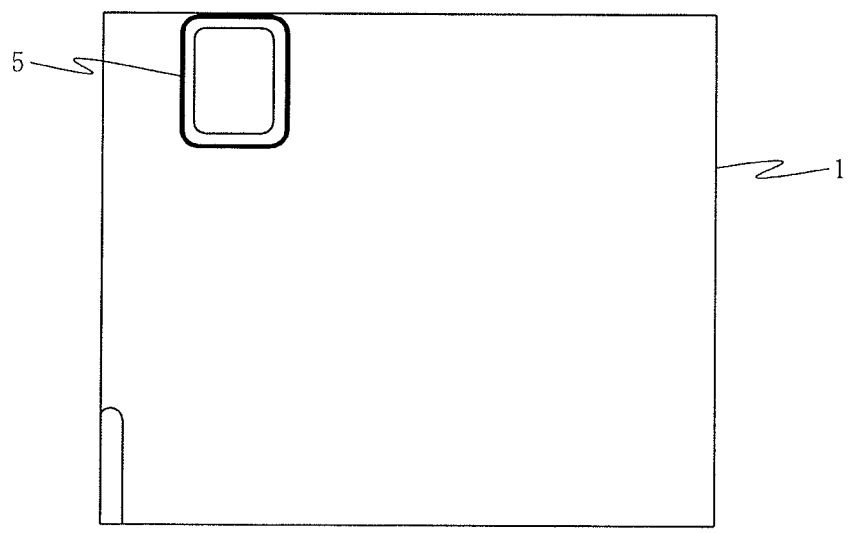
FIG. 14 is a defect image obtained through internal defect detection shown in FIG. 2, according to the second embodiment.
Figure 15:
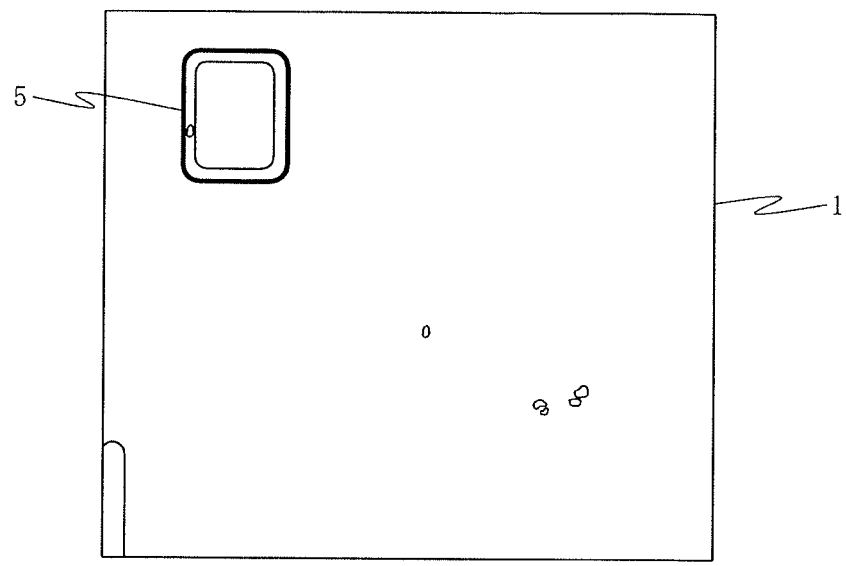
FIG. 15 is a binary image of the defect image in FIG. 14.
Figure 16:
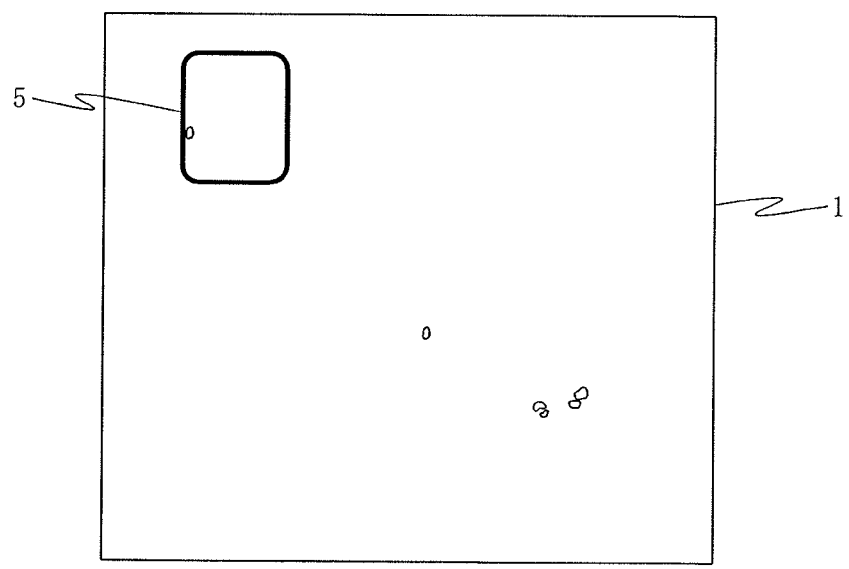
FIG. 16 is a view illustrative of an internal defect area calculated through image analysis of the binary defect image in FIG. 15.

FIG. 14 shows a defect image within the defect detection range of the aforementioned aluminum die cast part (column housing) 1 detected through ultrasonic inspection. Since the defect detection range is 90 mm along the height and an entirety of the inner circumference of the cylindrical section, as described above, the horizontal axis for the image is 119 mm long (inner diameter of the inner circumference: 38 mm), and the vertical axis is 90 mm long. FIG. 15 is a classified-by-color binary image obtained by binarizing the defect image based on an echo strength of 50% as a threshold value and classifying by color. Furthermore, FIG. 16 shows the results from conducting image analysis of each internal defect area no less than the echo strength of 50% shown in FIG. 15. Note that it was determined that internal defect areas with 50 pixels or less (areas of less than 0.2 mm$^2$) do not cause problem in strength, and therefore, they are eliminated from target areas to be evaluated.

Table 3 below gives all internal defect areas analyzed in such a manner. From all of them, an internal defect existing in the aforementioned high stress section (keylock section) 5 is No. 5 in Table 1. Note that if there are multiple internal defects in the high stress region (keylock section) 5, the largest internal defect area will be selected and evaluated.

TABLE 3

| No. | area | unit | perimeter | unit |
|---|---|---|---|---|
| 1 | 0.22 | mm$^2$ | 1.81 | mm |
| 2 | 0.25 | mm$^2$ | 1.83 | mm |
| 3 | 1.58 | mm$^2$ | 5.13 | mm |
| 4 | 0.35 | mm$^2$ | 2.08 | mm |
| 5 | 0.38 | mm$^2$ | 2.27 | mm |
| 6 | 0.20 | mm$^2$ | 2.02 | mm |
| 7 | 0.34 | mm$^2$ | 2.13 | mm |
| 8 | 0.24 | mm$^2$ | 1.68 | mm |
| 9 | 0.21 | mm$^2$ | 1.51 | mm |
| 10 | 0.19 | mm$^2$ | 1.43 | mm |
| 11 | 3.79 | mm$^2$ | 9.79 | mm |
| 12 | 1.98 | mm$^2$ | 6.48 | mm |
| 13 | 1.57 | mm$^2$ | 7.42 | mm |
| 14 | 0.90 | mm$^2$ | 4.29 | mm |
| 15 | 0.23 | mm$^2$ | 2.08 | mm |
| 16 | 0.24 | mm$^2$ | 1.90 | mm |
| 17 | 0.26 | mm$^2$ | 2.08 | mm |

In this manner, internal defects in ten aluminum die cast parts (column housing) 1 are detected through ultrasonic inspection, and the internal defect areas in the high stress regions (keylock section) 5 are analyzed. Furthermore, a torsion test is conducted on those aluminum die cast parts (column housings) 1, thereby detecting a breaking torque. Table 4 below gives a relationship between the internal defect area in the high stress region (keylock section) 5 and breaking torque load during a torsion test. Moreover, FIG. 17 is a graph showing the results given in Table 4.

TABLE 4

|  | No. | Defect area · [mm$^2$] | Breaking torque [Nm] |
|---|---|---|---|
| Working example | 1 | 0.00 | 383 |
|  | 2 | 0.00 | 379 |
|  | 3 | 0.38 | 372 |
|  | 4 | 0.52 | 374 |
|  | 5 | 0.71 | 372 |
|  | 6 | 0.75 | 365 |
|  | 7 | 0.92 | 313 |
|  | 8 | 1.05 | 289 |
|  | 9 | 1.21 | 259 |
|  | 10 | 1.33 | 240 |

As is apparent from FIG. 17, the larger the internal defect area in the high stress region (keylock section) 5, the smaller the breaking torque applied through the torsion test. That is, the larger the internal defect area in the high stress region (keylock section) 5, the earlier it is destroyed. However, if the internal defect area in the high stress region (keylock section) 5 is 0.8 mm$^2$ or less, an almost constant breaking strength is maintained irrelevant of the internal defect area. Namely, in the case of the aluminum die cast part (column housing) 1 of the embodiment, and if the internal defect area in the high stress region (keylock section) 5 is 0.8 mm$^2$ or less, it can be determined that it has a predetermined strength.

Moreover, according to observation of a destructive cross section of the actual aluminum die cast part (column housing,) since a crack has spread from an internal defect, it is determined as an internal defect-originated destruction. Therefore, size of the internal defect in the high stress region (clamp section) 5, that is, the internal defect area is detected, and if the internal defect area is equal to or less than a predetermined value, an internal defect-originated destruction will be prevented. Therefore, if the internal defect area in the high stress region (keylock section) 5 is equal to or less than a predetermined value, it will be appropriate to evaluate that the aluminum die cast part (column housing) 1 has a predetermined strength.

As such, according to the aluminum die cast part strength evaluating method of the embodiment, a predetermined range of the high stress section (keylock section) 5 in an aluminum die cast part (column housing) 1, which is detected through stress analysis beforehand, is subjected to ultrasonic inspection for an internal defect, and if the maximum internal defect area within the predetermined range is equal to or less than the predetermined value, it can be determined that the aluminum die cast part (column housing) 1 has a predetermined strength. Consequently, strength of the actual aluminum die cast part (column housing) 1 will be evaluated correctly.

Moreover, according to the aluminum die cast part of the embodiment, the aluminum die cast part (column housing) 1 with a predetermined strength will be obtained by evaluating strength using the method for evaluating strength of an aluminum die cast part according to the embodiment, and the maximum-possible internal defect area is set to 0.8 mm$^2$ or less within a predetermined range of the high stress region 5.

A method for detecting a defect of an aluminum die cast part strength of an embodiment according to the present invention is explained below referring drawings. For example, the aluminum die cast part 1 to be strength-evaluated according to the embodiment is a column housing of an electric power steering apparatus, as in the first embodiment. A movable 6-axis ultrasonic reflectoscope used for the method for evaluating strength of aluminum die cast part according to the embodiment, which is the same as in FIG. 1 of the first embodiment, scans spirally and detects an internal defect of the high stress region of the cylindrical section in the aluminum die cast part (column housing) 1 described later. In addition, X-ray computed tomography is also used to detect an internal defect. Note that as given in the first and the second embodiment, breaking strength of the aluminum die cast part 1 may be determined by detecting an internal defect in the high stress region of the aluminum die cast part 1 using ultrasonic reflectoscope, and evaluation based on the defect area.

Figure 18A:
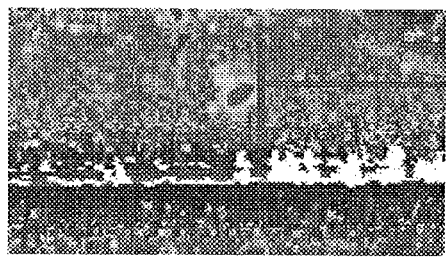
FIGS. 18A to 18D are images of a cold flake and a blowhole detected through ultrasonic inspection using an aluminum die cast part defect detecting method of an embodiment according to the present invention, and cross-sectional photographic images thereof.
Figure 18B:
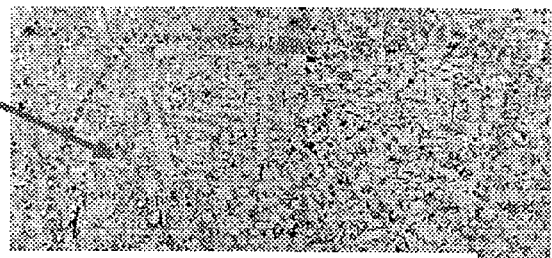
Figure 18C:
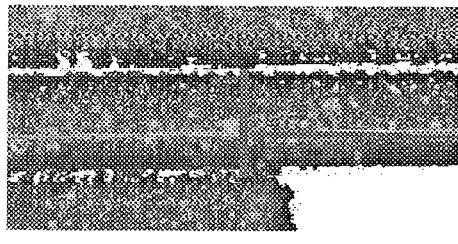
Figure 18D:
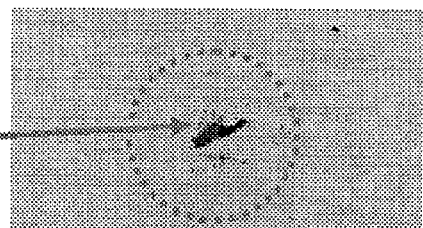

A method for detecting a detect of an aluminum die cast part defect inspecting method, according to the present invention includes, detecting an internal defect within a predetermined range including the aforementioned high stress region, calculating abundance of defects based on the sum total of defects and volume of the measuring range, and predicting a decrease in strength. In particular, if there is a defect in the high stress region A, decrease in strength is remarkable. A method for detecting a detect of an aluminum die cast part defect detecting method, according to the embodiment, will be explained below in detail along with the development procedure. First of all, an ultrasonic-inspected cross-sectional defect image of a cold flake in an aluminum die cast part is observed and verified. FIGS. 18A and 18B show a cold flake detected through ultrasonic inspection and a corresponding cross-sectional photographic image, respectively. It is known that a blowhole is detectable through ultrasonic inspection. FIGS. 18C and 18D show a blowhole detected through ultrasonic inspection and corresponding cross-sectional photographic image, respectively. As is apparent from the images, a cold flake and a blowhole in an aluminum die cast part are detectable through ultrasonic inspection. Note that, although not shown herein, an inclusion of the aluminum die cast part is also detectable through ultrasonic inspection.

On the other hand, because of the past records that cold flakes are undetectable through X-ray computed tomography while blowholes are detectable through the same, X-ray computed tomography and ultrasonic inspection are carried out, so as to obtain images of a blowhole and a cold flake using a flat test piece. The resulting images are shown in FIG. 19A. Note that UT in FIG. 19A represents Ultrasonic Testing, or ultrasonic inspection. Moreover, FIG. 19B shows a cross-sectional photographic image of a portion in which a cold flake is detected through ultrasonic inspection shown in FIG. 19A. Although a cold flake shown in FIG. 19B is recognized in the image portion in which the cold flake is detected thorough ultrasonic inspection, X-ray computed tomography could not detect the cold flake.

Next, a tensile test piece is created from the same aluminum material as the aluminum die cast part, and an internal defect of the parallel portion (test section) is detected through X-ray computed tomography and ultrasonic inspection. Once the internal defect is detected within, the tensile test piece is then subjected to tension test, and the fracture surface is then observed. The internal defect images of respective blowholes and cold flakes, which may lead to breakage and are detected through X-ray computed tomography and ultrasonic inspection, are verified. Two kinds of results are shown in FIG. 20A and FIG. 20B. FIG. 20A shows a breakage emanating from a blowhole, wherein the blowhole observed in the defect agrees with the internal defect images or blowhole images obtained through X-ray computed tomography and ultrasonic inspection. On the other hand, FIG. 20B shows breakage emanating from a cold flake, wherein the cold flake observed in the defect agree with the internal defect images obtained through ultrasonic inspection, or cold flake images. However, they do not agree with the internal defect images obtained through X-ray computed tomography. Note that, an inclusion of the aluminum die cast part is also detectable through X-ray computed tomography.

These results have given information that a sum total of defect areas of cold flakes may be found by subtracting sum total of the defect areas in the internal defect image obtained through X-ray computed tomography for detecting a blowhole (and an inclusion) from the sum total of the defect areas in the internal defect image obtained through ultrasonic inspection for detecting a blowhole and a cold flake (and an inclusion.) Therefore, defect areas in the same internal defect image obtained through ultrasonic inspection and X-ray computed tomography, should agree with each other for the same internal defect. Therefore, a circular hole 0.5 mm in diameter (i.e., an artificial defect) as shown in FIG. 21A is made on a cylindrical test piece cut out from an aluminum die cast part, and it is then subjected to X-ray computed tomography and ultrasonic inspection, acquiring respective images. FIG. 21B shows artificial defect images obtained through X-ray computed tomography, and FIG. 21C shows artificial defect images obtained through ultrasonic inspection. An artificial defect 0.5 mm in inner diameter is confirmed from the artificial defect image obtained through X-ray computed tomography. Regarding the artificial defect image obtained through ultrasonic inspection, since the size of a defect image can be adjusted through adjusting a threshold value for recognition of a defect, the threshold value is adjusted such that the inner diameter of the artificial defect becomes 0.5 mm, and adjustment of outputs of respective images obtained through X-ray computed tomography and ultrasonic inspection is completed.

In FIG. 22, internal defect images at the same location in an actual aluminum die cast part obtained through X-ray computed tomography and ultrasonic inspection, and arranged in line are shown. Regarding the blowhole areas, each being 0.2 mm² or larger, the defect image obtained through X-ray computed tomography agrees with that obtained through ultrasonic inspection. However, although a cold flake is detectable in the defect image obtained through ultrasonic inspection, it is not detectable in the defect image obtained through X-ray computed tomography. By taking an actual cross-sectional photograph of the upper part of the defect image of a cold flake obtained through ultrasonic inspection, a cold flake is confirmed as shown in FIG. 23.

Therefore, the internal defect image obtained through ultrasonic inspection is subjected to the following treatment. That is, a predetermined range of the aluminum die casting part is subjected to ultrasonic inspection, and the internal defect image obtained through ultrasonic inspection is binarized based on a predetermined threshold value, which is obtained by tuning outputs using a defect included test piece 0.5 mm in diameter, as shown in FIG. 24A, and an internal defect area of 0.2 mm² or larger, for example, is calculated using an image analysis software program, as shown in FIGS. 24B and 24C. In order to make it easier to understand, a histogram for every defect area in every test number of aluminum die cast part is created, as shown in FIG. 24D. A sum total of the defect areas in every test number of aluminum die cast part is calculated as an ultrasonic-inspected sum total of defect areas. The ultrasonic-inspected sum total of defect areas contains defect areas of a blowhole and a cold flake (and a defect area of an inclusion.)

Therefore, as shown in FIG. 25A, for example, a predetermined range of the cylindrical section in the aluminum die cast part is ultrasonic-inspected, the resulting detected values are binarized, as shown in FIG. 25B, an internal defect area of 0.2 mm² or larger is calculated, as shown in FIG. 25C, a predetermined range of the cylindrical section in the aluminum die cast part is subjected to X-ray computed tomography, internal defect images obtained through ultrasonic inspection and X-ray computed tomography are subjected to image analysis range for every test number within a predetermined range of the same region, as shown in FIG. 25D, and a sum total of defect areas is calculated as a defect sum total. In this case, it is determined that Nos. 1 to 3 are cold flakes and No. 4 is a blowhole. Subsequently, as shown in FIG. 25E, a sum total of cold flake areas within a predetermined range of the aluminum die cast part is calculated by subtracting the sum total obtained through X-ray computed tomography from the sum total obtained through ultrasonic inspection.

Note that, the reason why internal defect areas of 0.2 mm² or larger are selected is because of two reasons: one that internal defect areas below 0.2 mm² are expected to be strong enough, and the other that it is impossible to detect a defect area below 0.2 mm² correctly through X-ray computed tomography at the present. By ultrasonic inspection an internal defect area below 0.2 mm² can also be detected. Therefore, if the sum total obtained through X-ray computed tomography is simply subtracted from the sum total obtained through ultrasonic inspection without limitation of internal defect area to 0.2 mm² or larger, internal defect areas below 0.2 mm² obtained though ultrasonic inspection cannot be recognized, or whether it is a blowhole or a cold flake cannot be determined. As a result, even internal defect areas satisfactory in strength would be evaluated. Therefore, an evaluation method based on internal defect areas of 0.2 mm² or greater is established.

According to such an aluminum die cast part defect detecting method of the embodiment, each image output is adjusted beforehand such that artificial defect areas (from the same defect) in respective images obtained through ultrasonic inspection and X-ray computed tomography agree with each other; ultrasonic inspection is conducted over a predetermined range of the aluminum die cast part 1 for an internal defect; a defect detected through ultrasonic inspection over the predetermined range is subjected to image analysis, thereby finding the defect area; a sum total of internal defect areas within the predetermined range obtained through ultrasonic inspection is calculated as an ultrasonic-inspected sum total; an internal defect in the same predetermined range of the aluminum die cast part 1 is subjected to X-ray computed tomography; the internal defect detected through X-ray computed tomography over the predetermined range is subjected to image analysis, thereby finding the defect area; a sum total of internal defect areas obtained through X-ray computed tomography over the predetermined range is calculated as a X-ray computed tomography sum total; the X-ray computed tomography sum total is subtracted from the ultrasonic inspected sum total; and thereby calculating a sum total of cold flake areas within the predetermined range of the aluminum die casting part 1. As a result, the internal defect of the aluminum die cast part 1, especially the state of the cold flake may be detected correctly.

Moreover, for a sum total of internal defect areas detected through ultrasonic inspection and sum total of internal defect areas detected through X-ray computed tomography, a sum total of defect areas, each being equal to or larger than a predetermined area, is calculated, thereby further detecting the internal defect of the aluminum die cast part 1, especially the state of a cold flake, correctly.

Moreover, for a sum total of internal defect areas detected through ultrasonic inspection and sum total of internal defect areas detected through X-ray computed tomography, a histogram based on the number of the internal defects for a predetermined range of defect areas is created, allowing easy recognition of the state of an internal defect in the aluminum die cast part 1. Moreover, it is possible to confirm distribution of defect areas in the part based on the images acquired through ultrasonic inspection and X-ray computed tomography.

REFERENCE SIGNS LIST

1: ALUMINUM DIE CAST PART
2: TURNTABLE
3; PROBE
4: INTERNAL DEFECT
5: HIGH STRESS REGION

The invention claimed is:
1. A method for detecting a defect of an aluminum die cast part, the method comprising:
adjusting beforehand both outputs of an image obtained through ultrasonic inspection and an image obtained through X-ray computed tomography, so that defect areas corresponding to the same defect in the both images agree with each other;
conducting ultrasonic inspection for internal defect in a predetermined range of an aluminum die cast part;
obtaining an internal defect area through image analysis of an internal defect detected through the ultrasonic inspection over the predetermined range;

calculating a sum total of internal defect areas detected through the ultrasonic inspection over the predetermined range as a sum total of ultrasonic inspected defect areas;

conducting X-ray computed tomography over a predetermined range of the aluminum die cast part for an internal defect;

obtaining an internal defect area through image analysis of the internal defect detected through X-ray computed tomography over the predetermined range;

calculating a sum total of internal defect areas detected through X-ray computed tomography of the predetermined range as a sum total of X-ray computed tomography defect areas;

subtracting the sum total of X-ray computed tomography defect areas from sum total of the ultrasonic inspected defect areas; and calculating a sum total of cold flakes areas within a predetermined range of the aluminum die cast part.

2. A method for detecting a defect of an aluminum die cast part according to claim 1, wherein for finding a sum total of internal defect areas obtained through ultrasonic inspection and a sum total of internal defect areas obtained through X-ray computed tomography, a sum total of defect areas, each being equal to or greater than a predetermined area, is calculated.

3. A method for detecting a defect of an aluminum die cast part according to claim 1, wherein for finding a sum total of internal defect areas obtained through ultrasonic inspection and a sum total of internal defect areas obtained through X-ray computed tomography, a histogram for the number of internal defects within a predetermined defect area range is created.

4. A method for detecting a defect of an aluminum die cast part according to claim 2, wherein for finding a sum total of internal defect areas obtained through ultrasonic inspection and a sum total of internal defect areas obtained through X-ray computed tomography, a histogram for the number of internal defects within a predetermined defect area range is created.

* * * * *